United States Patent [19]
McCoy et al.

[11] 3,951,770
[45] Apr. 20, 1976

[54] HYDROCARBON CONVERSION

[75] Inventors: David R. McCoy, Wappingers Falls; Dennis R. Taylor, Poughkeepsie, both of N.Y.

[73] Assignee: Texaco Inc., New York, N.Y.

[22] Filed: July 5, 1974

[21] Appl. No.: 485,858

[52] U.S. Cl.............................. 204/163 R; 260/660
[51] Int. Cl.².................... B01J 1/10; C07C 17/10
[58] Field of Search............ 204/163 R; 260/654 H, 260/660

[56] References Cited
UNITED STATES PATENTS 2,998,459  8/1961  Baker et al. ............... 260/654 H X
3,790,462  2/1974  Schultz et al. .................. 204/163 R

*Primary Examiner*—Leland A. Sebastian
*Attorney, Agent, or Firm*—T. H. Whaley; C. G. Ries; Carl G. Seutter

[57] ABSTRACT

Chemical processing of normal-paraffin hydrocarbons may be carried out with increased selectivity by use of a normal-paraffin hydrocarbon reactant which is adsorbed on the surface of a solid adsorbent such as diatomaceous earth prior to treatment in a free-radial (eg photochemically) initiated reaction.

19 Claims, No Drawings

HYDROCARBON CONVERSION

FIELD OF THE INVENTION

This invention relates to hydrocarbon conversion. More specifically it relates to photochemically initiated processes characterized by high selectivity.

BACKGROUND OF THE INVENTION

As is well known to those skilled in the art, hydrocarbons may be converted to hydrocarbon derivatives containing functional groups (typified by halogen groups); and these may serve as a starting point for the preparation of further derivatives.

Terminally substituted alkanes (especially those with 8–18 carbons) derived from n-paraffins are valuable chemical intermediates in the production of fatty acids, amines, alcohols, esters, and sulfonates for use as detergents, fabric softeners, lubricant additives, plasticizers, etc. (F. Asinger, *Paraffins: Chemistry and Technology*, transl. B. J. Hazzard, Pergamon Press, Oxford, 1968, pp. 735–6). By contrast, secondary substituted paraffins derived from these same paraffins generally decompose to form olefins or are unreactive when attempts are made to transform them into alcohols, sulfonates, etc. (Asinger, p. 736; H. Krauch and W. Kunz, *Organic Name Reactions*, John Wiley, New York, 1964, p. 444; Jack Hine, *Physical Organic Chemistry*, McGraw-Hill, New York, 1962, Chapt. 6).

The treatment of n-paraffins, under a variety of reaction conditions to introduce e.g. chlorine, always gives rise to a mixture of 1-chloroalkanes and secondary chloroalkanes. Although there are physical methods (U.S. Pat. No. 3,426,086) for separating the two classes of compounds from one another and chemical means of separation are feasible utilizing the different orders of reactivity for these compounds (for examples, see Chem. Abstr. 62 11671 (1965); D. J. Hurley et al., I & E.C. Prod. Res. & Devel. 4 44 (1965), no attempts have been made to isolate the 1-chloroalkanes from such chlorination mixtures for use as chemical intermediates because the 1-chloro isomer is formed in very low selectivities. For example, chlorination of n-dodecane using a variety of chlorinating agents and reaction conditions gives only 11–13% selectivity of the monochloro product to 1-chlorododecane (G. A. Russell article in *Free Radicals Vol.* 1, J. K. Kochi, ed., John Wiley, N.Y., 1973).

Several attempts have been made to influence the position of chlorine atoms in an alkane chain by use of solid absorbents. Deno and co-workers (N. C. Deno, R. Fishbein, and C. Pierson, J. Am. Chem. Soc., 1451 (1970)) were able to increase the ω-selectivity for chlorination of a fatty acid by first chemisorbing the acid in ~3 wt. % concentration on neutral alumina. They reasoned that the acid molecules were rigidly aligned in parallel to one another causing only the ω-positions to be open to attack from $Cl_2$ gas molecules. Eli Perry (Eli Perry, J. Org. Chem. 35, 2053 (1970)) was able to modify the course of reaction between hexane and chlorine by pre-adsorbing the paraffin on a Linde 13X sieve. This caused an increased selectivity to 1-chloro-hexane (an increase in the relative reactivity of primary to secondary hydrogens in hexane towards $Cl_2$). This effect was presumed to be due to the molecular sieving properties of the zeolite and was sensitive to the pore size of the sieve.

It is an object of this invention to provide a novel process for selective conversion of hydrocarbons. Other objects will be apparent to those skilled in the art.

STATEMENT OF THE INVENTION

In accordance with certain of its aspects, the method of this invention may comprise adsorbing a normal paraffin hydrocarbon onto the surface of a solid particulate adsorbent;

chlorinating said normal paraffin hydrocarbon on said solid particulate adsorbent in the presence of a free-radical initiator thereby forming a product containing a 1-chloro normal alkane on said solid particulate adsorbent; and recovering said product containing said 1-chloro normal alkane.

DESCRIPTION OF THE INVENTION

The charge which may be treated by the process of this invention may be a normal (straight chain) paraffin hydrocarbon. These n-alkanes may be available in pure streams containing a single hydrocarbon or more typically in streams containing a plurality of n-alkanes.

The normal paraffin hydrocarbon charge which may be advantageously treated by the process of this invention may possess a hydrocarbon chain length of 6–22 carbon atoms, more typically about 10–16 carbon atoms — these latter being of substantial economic interest.

Illustrative of the charge n-paraffins which may be treated by the process of this invention may be the following:

n-hexane
n-heptane
n-octane
n-nonane
n-decane
n-undecane
n-dodecane
n-tridecane
n-tetradecane
n-pentadecane
n-hexadecane
n-heptadecane
n-octadecane
n-nonadecane
n-eicosane
n-heneicosane
n-docosane etc.

The charge may consist essentially of one component or more typically, it may contain a mixture of components. It may be identified e.g. as a $C_{10}$–$C_{14}$ fraction, as $C_{12}$ cut, a $C_6$–$C_{22}$ fraction, etc.

The preferred charge hydrocarbons may be those which are in liquid phase at the temperature of operation i.e. which are above their melting point and below their boiling point.

In practice of the process of this invention, chlorination of the charge normal paraffin or alkane may be effected in the presence of solid particulate adsorbent.

The solid particulate adsorbent should be essentially inert to the components of the reaction mixture infra including chlorine, hydrogen chloride, etc. It may be activated prior to use by heat or vacuum treatment or it may be used without activation.

It is however a feature of the process of this invention, which is particularly unexpected, that increased selectivity toward terminal chlorination of normal paraffins (containing no stongly adsorbing polar groups) may be achieved when the solid particulate is an adsorbent which may be substantially free of internal pores.

A solid particulate adsorbent, as the term is used in this description, refers to a solid substance which has an outer surface (including e.g. topologically contiguous "inner" surfaces or pores of a size larger than ca. 20 A) on which a gas or vapor tends to collect. Adsorbents may include substantially solid particles with irregularly or regularly interrupted outer surfaces. Alternatively (and less preferably) they may include particles having essentially smooth surfaces on regularly shaped supports such as spheres, cylinders, etc.

The adsorbents which may be used in practice of this invention are unlike zeolites or molecular sieves (which give undesirable results in terms of terminal selectivity); zeolites or molecular sieves are particularly characterized by the presence of uniform internal pores of molecular size and shape into which molecules may fit — and it is this factor which contributes to the shape selectivity and ability to base-exchange characteristic of zeolites.

The adsorbents which may be used in practice of the process of this invention may be typically characterized as non-shape-selective and non-zeolitic; and they may be substantially free of the molecularly sized and shaped uniform passageways which characterize zeolites or molecular sieves.

Illustrative of the preferred adsorbents may be the following: natural clays such as montmorillonite, synthetic aluminosilicates, charcoal, diatomaceous earths, commercial filter aids, high volume cellulose products, alumina, activated aluminas, powdered calcium silicates.

Specific illustrative materials may include the following:

A. A commercial diatomite filter aid (available as the speed plus brand of filter aid from the Dicalite Division of Grefco Inc.);

B. A Grade H silica gel having an average particle size of 74–600 microns and 720–760 $m^2/g$ surface area (available from Davison Chemical Company);

C. An adsorption alumina having a particle size distribution of 100% within the 80–200 mesh range (available from Fisher Scientific Company);

D. A graphite powder (available as the Grade 38 brand of graphite from Fischer Scientific Company);

E. A hydroxypropyl cellulose having a 1500–2500 Brookfield viscosity at 25°C (1% in water) and having 95% of the particles through 30 mesh and 99% through 20 mesh (available as the Klucel Type H brand of hydroxypropyl cellulose from Hercules Inc.);

F. An Attapulgus clay having an average particle size of 3 microns and a surface area of 125 $m^2/g$ (available as the LVM Grade Attasorb brand of Attapulgus clay from Minerals and Chemicals Company);

G. A synthetic calcium silicate having an average particle size of ca. 3 microns, a surface area of 95–200 $m^2/g$), (available as the Micro-cel brand from Johns-Manville Company);

H. A talc powder having an average particle size of ca. 0.80 microns (available as the Mistron vapor brand from Sierra Talc Corp);

I. A commercial activated bentonite clay adsorbent having a surface area of 275 $m^2/g$, and containing ca. 71% $SiO_2$ and 17% $Al_2O_3$ (available as the Filtrol Grade 1 brand from Filtrol Corp.;

J. A fullers earth having an average particle size of 160–250 microns, a surface area of 120–140 $m^2/g$, (available as the Attapulgus brand of fullers earth from Mineral and Chemicals Company);

K. A Grade G silica gel having an average particle size of 10–40 microns and containing 0.03% iron maximum (available from E. Merck Company);

L. A fumed silica having an average particle size of 0.01 microns (available as the Cab-O-Sil brand of fumed silica from Cabot Corp);

M. An acid activated Montmorillonite Clay containing ca. 60% $SiO_2$ and 17% $Al_2O_3$ (available as the K-306 brand of Montmorillonite Clay from Girdler Company);

N. A silica-alumina cracking catalyst having a surface area of 125 $m^2/g$ (available as the MS-B brand of silica-alumina fluid cracking catalyst from American Cyanamid Company);

O. A silicic acid having a particle size of 100 mesh, 5% minimum loss on drying, and 16% loss on ignition (available as the AR-100 mesh brand of silicic acid from Mallinckrodt Company);

P. A polyvinyl chloride powder having a specific viscosity of 0.30 (available as the Marvinol 24 brand of PVC from Uniroyal Corp);

Q. An acid-washed vermiculite having a surface area of ca. 800 $m^2/g$ and prepared by treating 50 parts of natural vermiculite with 1000 parts of 25% aqueous sulfuric acid at reflux for 6 hours, filtering, water washing, and activating at 300°C for 3 hours.

The preferred solid particulate may be one which has a light color which avoids undesirable overheating by adsorption of heat from the light source; and preferably it may have a reflection coefficient greater than about 0.1. Typical reflection coefficients may be greater than about 0.1 and preferably greater than 0.5, say about 0.8–0.9.

The preferred solid particulate may be diatomite filter aid (A of the table supra). Other preferred solid particulate adsorbents may be G, H, and I of the table supra.

The preferred solid particulates adsorbents which may be employed are characterized by high surface area per unit weight. Typical such solids may possess a surface area of at least about 20, typically 500–1000 preferably 100–800 square meters per gram. The typical particle size which may be preferably employed may be 0.01–1000, preferably 0.01–250, say about 10 microns.

In practice of the process of this invention, reaction may be carried out by contacting the charge normal paraffin hydrocarbon with the solid particulate whereby the paraffin hydrocarbon is adsorbed onto the surface of the solid particulate. Contact may be effected by passing the hydrocarbon charge over a bed of solid particulate. It may be effected by passing the charge through a bed of fluidized solid particulate. It may be effected by passing a solution (in a solvent) of charge hydrocarbon into contact with the solid particulate — the solvent being thereafter evaporated.

In one embodiment, it may be desirable to maintain a fluidized bed of solid particulate (fluidized as by inert gas such as nitrogen) into which the charge hydrocarbon is introduced in vapor phase or more preferably in liquid phase.

The amount of the charge hydrocarbon introduced into contact with the solid particulate may vary depending upon many factors — including the adsorptivity of the solid particulate. Typically it may be found that 100 parts by weight of solid particulate may adsorb 0.1–20 parts, preferably 0.1–5 parts, say 0.5–2 parts of hydrocarbon.

Reaction may be carried out at temperature ranging over a wide range - from below the melting point of the charge hydrocarbon to above the boiling point of the charge hydrocarbon. Preferably the temperature may be within the range at which the charge hydrocarbon is in liquid phase at ambient conditions. Although typical temperatures may be minus 20°C. to 200°C., it may be preferred to oerate at 50°C.–100°C., say 80°C. Typically no particular control of temperature need be present; the autogenous temperature, essentially balanced by the substantial equivalence of the exothermic heat of reaction and the heat losses from the system, may be typically constant within the desired range. Typical pressure of operation may be 0–200 psig, preferably 0–50, say 0 psig.

Although it may be possible to use chlorinating agents typified by sodium hypochlorite, hypochlorous acid, t-butyl hypochlorite, or various N-chloramines, it is found that the most preferred is chlorine gas. Although it may be possible to add the chlorine gas in solvent and/or with the charge hydrocarbon, in the preferred embodiment, the chlorine gas may be admitted directly into contact with the solid particulate bearing the adsorbed hydrocarbon.

Chlorine may be added to the reaction mixture in amount of 0.1–1 moles, preferably 0.1–0.5 moles, say 0.2–0.3 moles per mole of charge hydrocarbon.

In one embodiment, the solid particulate may be loaded with charge hydrocarbon by contacting the former with the latter in a suitable solvent such as carbon tetrachloride. The solvent may be a volatile solvent; and it may be substantially removed by evaporation e.g. in vacuo.

The solid particulate, bearing adsorbed hydrocarbon, may be fluidized as by inert nitrogen gas passing upwardly through the bed. Chlorinating agent may be admitted to the bed — typically by feeding it in with the fluidizing gas.

Although initiation of the free-radical reaction may be effected by use of e.g. peroxy compounds or by thermal initiation, it is preferably effected by use of visible or ultraviolet radiation.

During the reaction, the reaction is initiated by use of a free-radical initiation system such as addition of a peroxy compound (e.g. benzoyl peroxide or di-tertiarybutyl peroxide) or a thermal initiation. More preferably, the reaction mixture is subjected to the presence of electromagnetic radiation having a wave length of 1000 to 7000 angstroms units. It is preferred however that photochemical chlorination be carried out using electromagnetic radiation of about 2900–7000 angstrom units. This range embraces the visible spectrum having a wave length of about 4000–7000 angstrom units; and the ultra-violet spectrum having wave lengths less than about 4000 angstrom units and down to 1000–2900 angstrom units may be less preferred.

In the preferred embodiment, the spectrum may include the ultraviolet and the visible ranges, viz., about 2900 to about 7000 angstom units. It is found however that visible light (4000–7000 angstrom units) typically provides results which are substantially better than those obtained with ultraviolet (including X-ray) radiation and which are substantially better than those obtained with infra-red radiation. Accordingly the most preferred source of electromagnetic radiation is that obtained by the use of visible light having a wave length of about 4000–7000 angstrom units.

During the reaction, the by-product hydrogen chloride is produced. It is preferred that the reaction be carried out under substantially anhydrous conditions e.g. the reaction mixture preferably contains less than 0.1% water (based upon hydrocarbon charge). Preferably the reactants may be dried prior to use.

During the reaction the chlorination may be found to be extremely selective to terminal halogenation. In the chlorination of a normal paraffin such as n-dodecane, it may be found that conversion of 10–60, preferably 20–40, say about 30% may be achieved (Conversion is defined as the weight percent of charge hydrocarbon consumed during the reaction). The terminal selectivity (defined as the weight percent of the desired terminally mono-chlorinated isomer in the total mono-chlorinated isomers) may be 12%–30%, say 22%. Control runs, carried out in similar manner but not using the process of this invention may typically give selectivities of typically about 10%–11%.

The desired product may be readily recovered from the reaction mixture. The products may be desorbed by increasing the temperature of the reaction mixture, by decreasing the pressure of the reaction mixture, by solvent washing, by displacement with gas or liquid including e.g. fresh hydrocarbon charge, etc.

Product 1-chloroalkanes may be recovered from liquid product as by water washing to remove hydrogen chloride and chlorine followed by distillation to separate 1-chloroalkane from charge hydrocarbon and other chloroalkanes. Other techniques may be apparent to those skilled in the art.

DESCRIPTION OF SPECIFIC EMBODIMENTS

Practice of the process of this invention may be apparent to those skilled in the art from the following examples wherein (as elsewhere in the description) all parts are parts by weight unless otherwise stated.

EXAMPLE I

In this example which represents practice of the process of this invention, 25 grams of a commercial diatomite filter aid was slurried with a solution of 0.3g normal dodecane in 100 ml of carbon tetrachloride. The solvent was removed in vacuo and the solid including the adsorbed hydrocarbon placed in an ultraviolet photoreactor equipped with a 90 watt medium pressure arc tube which emits light having a wave length of 1850–3700 angstroms.

The solids were fluidized with nitrogen; and 2.7 equivalents (based upon charge hydrocarbon) of chlorine gas were introduced over 8 minutes. Product was then recovered by desorption in chloroform. Analysis showed that the product contained 78% of monochlorododecane of which 17.6% (terminal activity) was the desired 1-chlorododecane.

EXAMPLE II

In a control example under comparable conditions, but in the absence of the solid adsorbent, the terminal selectivity was only 10.6%.

EXAMPLES III–XIX

In each of the examples of this series which represent practice of the process of this invention, 0.5 grams of dodecane were adsorbed on 35 grams of noted solid adsorbent and the solid mixture stirred in a round bottom flask for 5 minutes for ambient temperature of 25°C in the presence of a standard 100 watt light source (emitting light in the visible spectrum, including some ultraviolet, having a wave length of 2900–7000).

In each case the product obtained, after work-up as in Example I, was analyzed.

The following table sets forth the adsorbent, the conversion (weight percent of charge hydrocarbon consumed) and the terminal selectivity (weight percent of 1-chlorododecane in the monochlorododecane fraction):

| Example | Adsorbent | Selectivity |
|---|---|---|
| III | B | 20 |
| IV | C | 21.1 |
| V | D | 13.7 |
| VI | E | 12.7 |
| VII | A | 23.7 |
| VIII | F | 13.3 |
| IX | G | 27.0 |
| X | H | 24.4 |
| XI | I | 18.7 |
| XII | J | 15.6 |
| XIII | K | 14.6 |
| XIV | L | 15.9 |
| XV | M | 14.0 |
| XVI | N | 13.5 |
| XVII | O | 19.7 |
| XVIII | P | 12.1 |
| XIX | Q | 15.1 |

EXAMPLE XX

In a comparable control example, liquid n-dodecane was chlorinated at ambient temperature of 25°C in the presence of the same light source to give a terminal selectivity of 10.5%–11.5%.

EXAMPLES XXI–XXIII

The process of Example I was duplicated except that different adsorbents and temperatures (°C) were employed. The results were as follows:

| Example | Adsorbent | Temp. | Selectivity |
|---|---|---|---|
| XXI | H | 0 to −5 | 16.5 |
| XXII | H | 40° | 14.2 |
| XXIII | I | 5 to −8 | 16.6 |

EXAMPLES XXIV–XXVII

In this series of examples, the process of Example I was duplicated except that (i) different adsorbents were employed and (ii) the concentration of dodecane was varied. The results are as follows:

| Example | Adsorbent | Wt.% Dodecane | Selectivity |
|---|---|---|---|
| XXIV | B | 0.36 | 16.4 |
| XXV | G | 2.0 | 20.8 |
| XXVI | I | 0.7 | 19.3 |
| XXVII | M | 2.1 | 14.1 |

Results comparable to the above may be obtained by using the following illustrative charge hydrocarbons:

| Example | Hydrocarbon |
|---|---|
| XXVIII | n-decane |
| XXIX | n-octane |
| XXX | n-tetradecane |
| XXXI | A $C_{10}$ to $C_{14}$ waxy fraction containing n-paraffins and other paraffins |

EXAMPLES XXXII–XXXVI

In the following control experiments, various commercially available zeolites or molecular sieves (which are not adsorbents within the scope of this invention) were employed at reaction conditions comparable to those of Example I.

| Example | Weight Dodecane (g) | Zeolite (Wt. in g) | Reaction Conditions | Moles $Cl_2$ Mole Dodecane | Terminal Selectivity % |
|---|---|---|---|---|---|
| XXXII* | 2.47 | hydrogen mordenite (26.2) | u.v. light, room temp. | 0.48 | 10.5 |
| XXXIII* | 4.4 | Ca A (Linde 5A) (35.6) | u.v. light, room temp. | 0.54 | 11.8 |
| XXXIV* | 0.76 | sodium mordenite (27.2) | u.v. light, room temp. | 3.1 | 10.7 |
| XXXV | 1.0 | dealuminized mordenite (silica/alumina ratio 9 5) (11.5g) | visible light, room temp. | 0.24 | 13.1 |
| XXXVI | 0.5 | Na A (Linde 4 A) (35) | visible light, room temp. | 1.2 | 11.9 |

*In these runs, recovery of liquid products was less than 50 wt %, quantitative recoveries were obtained in all runs on non-zeolitic adsorbents.

From the above table, it will be apparent that the novel process of this invention permits attainment of unexpectedly high terminal selectivity. Specifically the terminal selectivities attained by use of the control molecular sieves is 10.5%–13.1%, averaging only 11.6.

In contrast, the experimental Examples carried out in practice of the instant invention gives yields as high as 27.0% (Example IX) and are generally substantially higher than those attained by the prior art.

It is particularly unexpected to find that solid particulate adsorbents may be employed in practice of the process of this invention. Such materials are characterized by their availability, cheapness, and strength. In particular they are unique in that they permit attainment of unexpectedly higher selectivity than is attained by the use e.g. of the substantially more expensive molecular sieves.

Although this invention has been illustrated by reference to specific embodiments, it will be apparent to those skilled in the art that various changes and modifications may be made which clearly fall within the scope of this invention.

We claim:

1. The method which comprises
    adsorbing a normal paraffin hydrocarbon onto the surface of a solid particulate adsorbent;

chlorinating said normal paraffin hydrocarbon on said solid particulate adsorbent in the presence of a free-radical initator thereby forming a product containing a 1-chloro normal alkane on said solid particulate adsorbent; and recovering said product containing said 1-chloro normal alkane.

2. The method of claim 1 wherein said normal paraffin hydrocarbon contains 6–22 carbon atoms.

3. The method of claim 1 wherein said normal paraffin hydrocarbon contains 10–16 carbon atoms.

4. The method of claim 1 wherein said normal paraffin hydrocarbon includes normal dodecane.

5. The method of claim 1 wherein said reaction is carried out in the presence of electromagnetic radiation.

6. The method of claim 1 wherein said reaction is carried out in the presence of electromagnetic radiation of wave length of 1000–7000 angstroms units.

7. The method of claim 1 wherein said reaction is carried out in the presence of electromagnetic radiation of wave length of 2900–7000 angstrom units.

8. The method of claim 1 wherein said reaction is carried out in the presence of visible light.

9. The method of claim 1 wherein said reaction is carried out in the presence of visible light of wave length of 4000–7000 angstrom units.

10. The method claimed in claim 1 wherein said reaction is effected with chlorine.

11. The method of claim 1 wherein said reaction is initiated by a peroxy compound.

12. The method of claim 1 wherein said reaction is initiated by a peroxy compound selected from the group consisting of benzoyl peroxide and di-tertiary-butyl peroxide.

13. The method of claim 1 wherein said reaction is initiated by thermal initiation.

14. The method of claim 1 wherein said reaction is carried out in the presence of solid particulate adsorbent having a surface area of 20–2000 square meters per gram.

15. The method of claim 1 wherein said reaction is carried out in the presence of a solid particulate adsorbent having a reflectivity of greater than about 0.1.

16. The method of claim 1 wherein said reaction is carried out in the presence of a solid particulate adsorbent containing at least one composition selected from the group consisting of clay
aluminosilicate
charcoal
diatomaceous earth
filter aids
alumina
calcium silicate
silica gel
graphite
cellulose
activated clay
talc
fuller's earth
fumed silica
silicic acid and
vermiculite 17. The method which comprises adsorbing a normal $C_6$ to $C_{22}$ paraffin onto the surface of a solid particulate adsorbent having a surface area of at least about 20 square meters per gram;

chlorinating, with chlorine gas, said normal $C_6$ to $C_{22}$ paraffin hydrocarbon adsorbed on said solid particulate, in the presence of visible light or ultraviolet light, thereby forming a product containing a 1-chloro normal alkane on said solid particulate; and recovering said product containing said 1-chloro normal alkane.

18. The method which comprises adsorbing a normal paraffin hydrocarbon onto the surface of a non-zeolitic solid particulate adsorbent;

chlorinating said normal paraffin hydrocarbon on said non-zeolitic solid particulate adsorbent in the presence of a free-radical initiator thereby forming a product containing a 1-chloro normal alkane on said non-zeolitic solid particulate adsorbent; and recovering said product containing said 1-chloro normal alkane.

19. The method which comprises adsorbing a normal paraffin hydrocarbon onto the surface of a non-zeolitic solid particulate adsorbent;

chlorinating said normal paraffin hydrocarbon on said non-zeolitic solid particulate adsorbent in the presence of a free-radical initiator thereby forming a product containing a 1-chloro normal alkane on said non-zeolitic solid particulate adsorbent; and adding chlorine to chlorinating step in amount of 0.1–1 moles of chlorine per mole of charge hydrocarbon; and recovering said product containing said 1-chloro normal alkane.

\* \* \* \* \*